United States Patent [19]

Diephouse et al.

[11] Patent Number: 4,915,875
[45] Date of Patent: Apr. 10, 1990

[54] OXIDATION PRODUCTS OF PARAMETHYL-SUBSTITUTED HINDERED PHENOLS

[75] Inventors: Timothy R. Diephouse; Robert M. Strom, both of Midland, Mich.

[73] Assignee: The Dow Chemical Company, Midland, Mich.

[21] Appl. No.: 926,693

[22] Filed: Nov. 4, 1986

Related U.S. Application Data

[63] Continuation of Ser. No. 762,668, Aug. 5, 1985, abandoned, which is a continuation-in-part of Ser. No. 606,482, May 3, 1984, abandoned.

[51] Int. Cl.$^4$ .................... C07C 41/06; C07C 45/38; C07C 46/02; C07C 50/30; C07C 67/04; C07C 69/16
[52] U.S. Cl. .................. 552/304; 260/410.5; 558/335; 558/339; 558/340; 560/8; 560/106; 560/186; 560/188; 560/221; 560/254; 564/389; 568/430; 568/432; 568/435; 568/607; 568/644; 568/662; 568/764; 568/774
[58] Field of Search ............ 260/396 R, 396 N, 410.5; 560/254, 8, 106, 188, 762, 668, 186, 221; 564/389; 568/432, 662, 435, 430, 644, 607, 764, 774; 558/335, 339, 340

[56] References Cited

U.S. PATENT DOCUMENTS 3,213,114 10/1965 Braxton, Jr. et al. .......... 260/396 N
4,119,671 10/1978 Bauer et al. ..................... 562/477
4,429,163 1/1984 Nishizawa et al. ............. 568/432

OTHER PUBLICATIONS

Filar, Tetrahedron Letters, No. 25, pp. 9–16, 1960.
Cook et al., "Oxidation of Hindered Phenols", pp. 3797–3799, (1956).
Balogh et al., J. Org. Chem., 36(10), pp. 1339–1341, 1971.
Macomber, J. Org. Chem., 47, pp. 2481–2483, (1982).
Olmura, J. Org. Chem., 49, pp. 3046–3050, (1984).

*Primary Examiner*—Vivian Garner

[57] ABSTRACT

Paramethyl-substituted hindered phenols are selectively oxidized by contacting with an oxidizing agent at elevated temperatures in the presence of a heterogeneous oxidative coupling catalyst. In the absence of an optional nucleophile the products comprise carbon-carbon oxidative coupling products. In the presence of a nucleophile, addition products result that may be further oxidized by continued exposure to the oxidizing agent to yield substituted p-hydroxybenzaldehydes.

24 Claims, No Drawings

OXIDATION PRODUCTS OF PARAMETHYL-SUBSTITUTED HINDERED PHENOLS

REFERENCE TO RELATED APPLICATION

This is a continuation of application Ser. No. 762,668, filed Aug. 5, 1985, now abandoned, which is a continuation-in-part of application Ser. No. 606,482, filed May 3, 1984, now abandoned.

BACKGROUND OF THE INVENTION

The present invention relates to the oxidation of p-methyl-substituted hindered phenols. More particularly, the present invention relates to a process for the heterogeneous oxidation of p-methyl-substituted phenols that is flexible in operation allowing the selective preparation of various oxygenated organic products including nucleophilic addition products and coupled reaction products. The latter class of coupled reaction products includes substituted stilbenequinones and reduced reaction products thereof.

Processes for the preparation of substituted stilbenequinones from phenolic compounds employing chemical oxidizing agents have been previously described. V. Balogh et al., *J. Org. Chem.*, 36, 1339 (1971) described such a process employing as an oxidizing agent silver carbonate on celite. The substituted stilbenequinones prepared by the process were reduced to the corresponding 4,4'-dihydroxystilbenes by use of zinc and acetic acid.

The addition of nucleophiles to intermediate species formed by oxidation of phenols is previously known. C. D. Cook et al., *J.A.C.S.*, 78, 3797 (1956) reported the preparation of benzyl radicals by oxidation of substituted p-methylphenols with alkaline ferricyanide or lead dioxide. Dimeric products as well as electrophilic addition products from the addition of nucleophiles, e.g., alcohols, were also reported.

Similarly, L. J. Filar, *Tet. Lett.*, (25), 9–16 (1960) reported the preparation of quinone methides from p-methyl phenols by action of a base such as triethylamine or by quantitative amounts of silver oxide or lead oxide. The mechanism was assumed to require the formation of an aryloxy radical. Reaction products in the absence of nucleophiles were dimeric materials. In the presence of nucleophilic reactants such as alcohols or carboxylic acids, addition products were formed.

Braxton et al., U.S. Pat. No. 3,213,114 (1965) disclose that the oxidation of 2,6-di-tert-butyl-4-methylphenol is problematical, leading to the formation of an extensive variety of products. Thus, in their invention directed to the preparation of p-benzoquinones, they teach that it is necessary that each of the 2,4 and 6 substituents on 2,4,6-trihydrocarbyl-substituted phenols be tertiary (i.e., having no hydrogen atoms attached to the carbon directly bonded to the phenol ring).

Bauer et al., U.S. Pat. No. 4,119,671 (1978) teach the preparation of salicylaldehyde and other hydroxybenzaldehydes by oxidation of a hydroxybenzyl alcohol with a platinum and lead-, silver-, tellurium- or tin-activated catalyst in an aqueous alkaline solution.

Nishizawa et al., U.S. Pat. No. 4,429,163 (1984) teach the preparation of certain 4-hydroxybenzaldehydes from oxidizing corresponding 4-methylphenols with a cobalt catalyst in solvents stable to oxygen and capable of dissolving the starting material, preferably such as alcohols, hydrocarbons, ethers, halogenated hydrocarbons and amines.

Each of the foregoing references is hereby incorporated by reference.

What is lacking and what is needed is a process for the selective heterogeneous catalytic oxidation of organic 4-methyl-substituted hindered phenols. By hindered is meant that there are any of a broad variety of substituents on at least the 2 and 6 positions of the phenol ring.

SUMMARY OF THE INVENTION

According to the present process, organic p-methyl-substitute hindered phenols, including those corresponding to the formula:

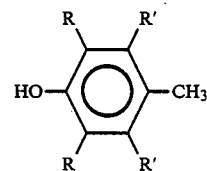

wherein R is independently each occurrence halogen or a substituent of up to 6 carbons selected from the group consisting of alkyl, alkenyl, haloalkyl and alkoxy and R' each occurrence independently is hydrogen or independently R, are oxidized by contacting with an oxidizing agent in the presence of a heterogeneous oxidation catalyst under conditions such that an oxygenated organic compound is selectively prepared.

The process results in the formation of an intermediate transient species thought to be a quinone methide. The rate of formation of the transient species may vary depending on the identity of the p-methyl-substituted hindered phenol, the concentration of the p-methyl-substituted hindered phenol and the presence or absence of other reactive species. Accordingly, the present inventors state the above concerning the identity of the intermediate species as their belief, but because the same is not necessary to a complete understanding of how to use the present invention, it being sufficient that the process performs as described, the present inventors do not wish to be bound by any particular theory of operation.

The present method for oxidizing p-methyl-substituted hindered phenol may be employed in processes for the selective preparation of a wide variety of useful oxygenated organic compound. In the absence of nucleophilic species, oxidation of p-methyl-substituted hindered phenols according to the present process results in the preparation of coupled compounds of substituted stilbenequinones, which thereafter may be reduced to prepare substituted stilbenes as well as substituted hydroxyphenylethanes depending on the degree of reduction performed. In the presence of a nucleophile, the present process allows for the preparation of the corresponding nucleophile substitution product. Continued exposure of these products to oxidation conditions in the presence of the heterogeneous oxidation catalyst preferably results in further oxidation to form a substituted hydroxybenzaldehyde product. Thus, the present invention may be employed as part of the overall preparation of substituted p-hydroxybenzaldehyde from hindered p-methylphenols.

The above products are useful industrial chemicals, e.g., antioxidants, and may be converted to polymers useful as molding resins. In addition, stilbene derivatives prepared by the present process are useful in the manufacture of dyes and as optical brighteners.

DETAILED DESCRIPTION OF THE INVENTION

The p-methyl-substituted hindered phenols for use in the present process are well-known or may be prepared by well-known techniques. Preferred reactants are substituted p-methyl phenols wherein at least 2 alkyl groups are in the 2 and 6 positions and all alkyl substituents have at most 6 carbons. Examples include 2,4,6-trimethyl phenol, 2,6-ditertiarybutyl-4-methyl phenol, 2,4,6-trimethyl-3,5-dibromophenol, 2,6-dimethoxy-4-methylphenol, etc. Also preferred are p-methyl-substituted hindered phenols wherein R is independently each occurrence halogen or a substituent of up to 6 carbons selected from the group consisting of alkyl, alkenyl, haloalkyl and alkoxy, at least one of which carbon atoms directly attached to the phenol ring is also directly attached to at least one other atom other than carbon (i.e., is a secondary carbon atom). More preferably, the carbon atom is also directly attached to no other carbons (i.e., is a primary carbon atom) and most preferably the carbon atom is methyl. An especially preferred reactant is 2,4,6-trimethylphenol.

The heterogeneous oxidation catalysts for use in the present process include the noble metals, i.e., gold, silver, platinum, palladium, ruthenium, iridium, osmium, mercury and rhodium. Also included are nickel, cobalt, chromium, lead and copper. The various heterogeneous catalysts are employed in an oxidative state suitable for the preparation of carbon-carbon coupled reaction products. For example, in the use of noble metal oxidation catalysts, the catalytic species is considered to be the corresponding noble metal oxide.

Of the previously-named heterogeneous oxidative catalysts, preferred are platinum, palladium, ruthenium, iridium, osmium and rhodium catalysts. More preferred are platinum and palladium catalysts. Platinum is the most preferred catalyst metal.

It is preferred that the catalyst have a large surface area. For this purpose, the catalyst may be employed in a highly comminuted or dispersed phase. Preferably the catalyst is deposited as a thin layer onto a support having a large surface area. Suitable areas are generally from about 10 m$^2$/g to about 1500 m$^2$/g or more. Preferred supports have a surface area from about 100 m$^2$/g to about 1000 m$^2$/g, suitable supports include clays, alumina, zeolites, carbon or activated charcoal. Preferred catalyst supports are carbon or activated charcoal.

The catalyst metal is present at any level sufficient to catalyze the reaction. Preferably, levels of catalysts metal on the support are from about 0.5 percent by weight of the supported catalyst to about 20 percent by weight. Preferable amounts of catalyst used in the process are from about 2 percent to about 20 percent by weight of the p-methyl-substituted hindered phenol as in a batch process.

The oxidizing agent comprises a suitable source of elemental oxygen. Examples include aqueous solutions of hydrogen peroxide, ozone, gaseous oxygen, a mixture of oxygen and an inert gas such as nitrogen, air, etc. A preferred oxidizing agent comprises gaseous oxygen or mixtures thereof employed at atmospheric or at elevated pressures above atmospheric pressure. Preferred oxygen pressures or partial pressures when mixtures are involved are from about 25 psig (172.4 kPa) to about 1000 psig (6895 kPa). Most preferred pressures are from about 100 psig (689.5 kPa) to about 750 psig (5171.25 kPa).

During the reaction it is important that the catalyst surface be "activated" towards preparation of oxidation products. When gaseous oxygen is employed as the oxidizing agent, activation is accomplished by maintaining the catalyst surface in an oxygen-rich environment. Due to the additional presence of liquids in the reaction mixture and the formation of a liquid film on the surface of the catalyst, oxygen starvation at the catalyst surface can occur especially when operating at atmospheric pressure. However, vigorous stirring or agitation of the reaction mixture can act to efficiently transfer oxygen to the catalyst surface. Accordingly, especially in the absence of elevated pressure, the reaction is preferably conducted with stirring. Increasing the activation increases selectively to the substituted products in the presence of the nucleophiles.

The reaction is conducted at elevated temperatures. Preferred temperatures are from about 25° C. to about 150° C., most preferred temperatures are from about 25° C. to about 110° C. In addition, selectivity to the substituted products is preferably favored by temperatures from about 50° C. to about 110° C., more preferably from 70° C. to about 90° C. Also, selectivity to the coupled compounds is preferably favored by temperatures from about 25° C. to about 80° C., more preferably from about 25° C. to about 40° C. Generally, under the above reaction conditions, reaction time of one or more hours up to about 6 hours are sufficient, however, longer or shorter reaction periods may be employed if desired.

The process may be operated with or without a solvent. In the absence of additional solvent, also referred to as a liquid reaction medium, the substituted p-methyl phenol may act as a solvent. Preferably, however, an additional quantity of an inert liquid is employed as an aid in transport of reactants and recovery of the product. Any liquid that, under the reaction conditions employed remains unreactive and retains the reactor contents in a fluid state, may be employed. Suitable inert liquids are aromatic compounds such as alkylated aromatics or halogenated aromatics and mixtures thereof. Preferred inert solvents are toluene, ethylbenzene or diethylbenzenes.

As previously discussed, the reaction products of the present invention may be conveniently varied according to the presence or absence of a nucleophile. In the presence of a nucleophile, nucleophile substitution products are obtained which may subsequently rearrange to form a substituted hydroxybenzaldehyde. In the absence of a nucleophile, the primary reaction product is the corresponding coupled compound, i.e., a stilbenequinone or reduced derivative thereof.

Selectivity to either coupled or nucleophile substitution products is preferably about 60 percent or above of the total yield of the p-methyl-substituted hindered phenol, more preferably about 70 percent or above and most preferably about 80 percent or above. It is especially preferred that the selectivity is about 90 percent or above.

The variety of reaction products obtained by means of the present invention are illustrated by reference to the following schematic illustration.

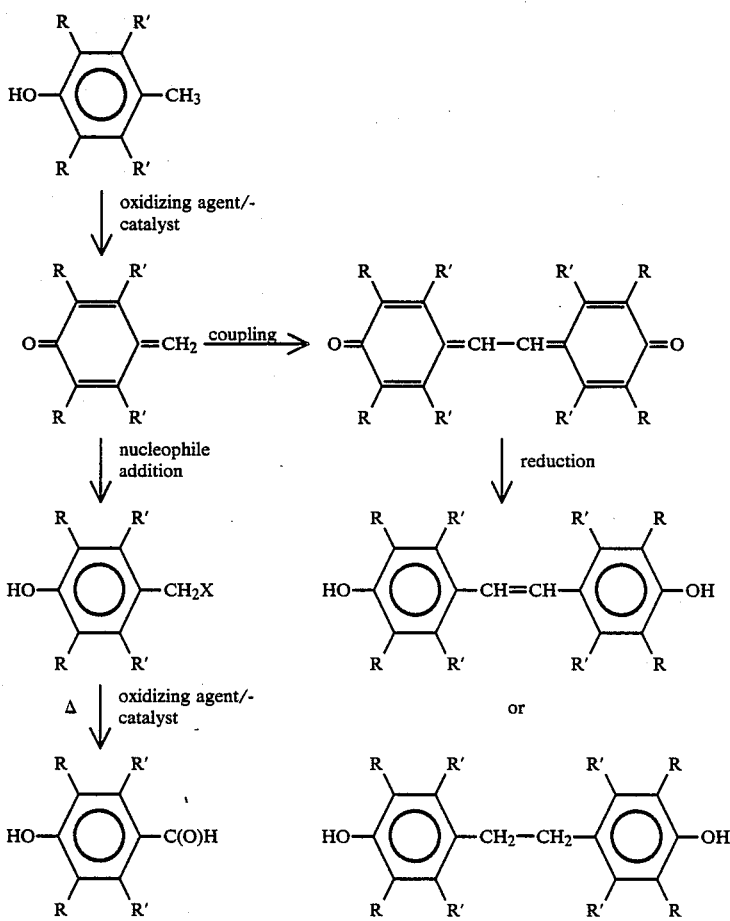

In the above illustration X is a remnant of a nucleophile. Suitable examples of X include halo, cyano, —OC(O)R, —OR or —OH, where R is a moiety of up to 20 carbons selected from the group consisting of alkyl, hydroxyalkyl, alkenyl, aryl, alkaryl, alkenylaryl or (CH$_2$CHR'O)$_n$R', where R' is hydrogen or lower alkyl.

In the embodiment of the invention whereby a nucleophile is added to the reaction mixture, suitably, at least about a stoichiometric amount of the nucleophile and preferably from about 1 to about 5 moles compared to the number of moles of p-methyl-substituted phenol are added.

As previously mentioned, suitable nucleophiles include aliphatic nucleophilic reagents having up to about 20 carbons including carboxylic acids, acid anhydrides, amines, alcohols, diols, polyols, phenols, (poly)alkylene glycols, and (poly)alkylene glycol ethers, as well as hydrogen cyanide, hydrogen halides and water. During the addition process, the reaction conditions need not be altered compared with those reaction conditions employed in the coupling reaction, excepting as to the addition of the nucleophile. Where the nucleophilic reactant is a liquid, it may be employed as a solvent in place of at least some of the additional inert liquids previously named herein. Gaseous nucleophilic reactants such as hydrogen cyanide or hydrogen halides are best added in a controlled manner to the liquid reaction medium.

The nucleophilic substitution product prepared by the present invention may be recovered if desired, and employed without further treatment, as e.g., a solvent or antioxidant, etc. Additionally the compounds may be further modified for the preparation of additional commercial products such as molding resins. However, it has now been discovered by the present inventors that the substituted methylene moiety resulting from the nucleophilic substitution may be expeditiously converted to an aldehyde moiety under further exposure to oxidizing conditions. Specifically, merely contacting the initial nucleophilic substitution product with the heterogeneous oxidation catalysts under oxidizing conditions as hereinbefore described results in the formation of hindered p-hydroxy-substituted benzaldehydes.

Preferred aliphatic nucleophilic reagents for the above process include carboxylic acids, alcohols and (poly)alkylene glycol. Water is another preferred nucleophile, especially when not alkalized. Most preferred aliphatic nucleophilic reagents are ethylene glycol and acetic acid.

In the operation of the invention, the heterogeneous oxidative coupling catalyst is placed into a suitably designed reactor vessel fitted with a reactant inlet and product outlet along with heating means as well as an entrance and exit means for the oxidizing agent. The reactor vessel is charged with a solution of the p-methyl-substituted hindered phenol optionally in the previously described liquid reaction medium. In a batch operation, the reactor is then heated to the desired reaction temperatures accompanied by addition of oxidizing agent. Agitation, as for example by stirring, may also be employed. In a continuous operation, the reactant charge is supplied to a reactor containing the catalyst that is maintained at the desired temperature. A stream of oxidizing agent, i.e., oxygen-containing gas is also supplied to the reactor either concurrently or countercurrently and the product mixture is continuously removed.

In the absence of a nucleophile, the substituted stilbenequinone in the product mixture is separated from unreacted p-methyl-substituted hindered phenol if necessary and may even be separated from the liquid reaction medium as by distillation or precipitation. Additionally, in the reaction mixture there may be small amounts of partially oxidized products, especially the corresponding 4,4'-dihydroxystilbene. Where the desired product is the corresponding substituted bishydroxyphenyl ethane, the presence of under-oxidized by-products is immaterial, since both the stilbenequinone and stilbene may be reduced to the desired bishydroxyphenyl ethane.

The reduction may be accomplished by any suitable technique. Preferably, the unseparated crude reaction mixture containing substituted stilbenequinone is contacted with a heterogeneous hydrogenation catalyst maintained under reducing conditions. Suitable hydrogenation catalysts include noble metals, nickel, copper or other known heterogeneous reduction catalysts. A preferred reduction catalyst is the reduced form of the oxidative coupling catalyst employed for the oxidative coupling process. By employing the reduced form of the oxidative coupling catalyst for the reduction the oxidation and reduction may be performed in one vessel without the need to change catalysts. The reaction conditions employed to effect hydrogenation are substantially modified from the oxidative coupling conditions initially employed. Generally, the hydrogenation is conducted at temperatures from about 25° C. to about 150° C. and pressures from about atmospheric to about 100 psig (689.5 kPa) in the presence of a hydrogen-containing gas. Preferred hydrogenation catalysts are palladium and platinum metals which under the stated hydrogenation conditions are believed to be in the elemental form.

The hydrogenated reaction product is readily recovered by filtration. Separation of catalyst may be accomplished by filtering the hot, molten product. Repeated crystallization or other technique may be employed for purification. In the presence of a nucleophile, the desired nucleophile substitution product is easily recovered by first separating the catalyst, then extracting or merely evaporating the solvent if a solvent is present. Purification may be accomplished by distillation or other suitable technique.

SPECIFIC EMBODIMENTS

Having described the invention, the following examples are provided as further illustrative of the invention and are not to be construed as limiting.

EXAMPLE 1

Into a 300-ml stainless steel stirred autoclave is placed 10 g of 2,4,6-trimethyl phenol, 1 g of 5 percent palladium on carbon (50 percent water by weight) and 30 ml of diethylbenzene. The reactor is pressurized to 350 psig (2413.25 kPa) with O₂ and heated to 70° C. The reactor is held at this temperature for 2 hours at which time substantial amounts of 3,3',5,5'-tetramethyl stilbenequinone are present. The reactor is then flushed with N₂ and repressurized with 40 psig (275.8 kPa) of H₂. Once repressurized, the reactor is heated to 130° C. and held at this temperature for 2 hours. The reaction material is filtered while hot to remove the catalyst. The reaction mixture is then analyzed by gas-liquid chromatography. Conversion of 2,4,6-trimethyl phenol is 84 percent with a selectivity to 1,2-bis-(3,5-dimethyl-4-hydroxyphenyl)ethane of 67 percent.

EXAMPLE 2

The reaction conditions of Example 1 are substantially repeated employing 0.5 g of additional heterogeneous catalysts further identified in Table 1. The reaction is conducted in oxygen at 350 psig (2413.25 kPa) employing diethylbenzene solvent a reaction temperature of 50° C. and a reaction time of one hour. The hydrogenation is performed with the same catalyst under hydrogen atmosphere at 40 psig (275.8 kPa) using the initial charge of diethylbenzene solvent, at 120° C. for 2 hours. In all cases the products are found to comprise 1,2-bis-(3,5-dimethyl-4-hydroxyphenyl)ethane and oligomeric products thereof. Results are contained in Table 1. Selectivity is based on 1,2-bis(3,5-dimethyl-4-hydroxyphenyl)ethane.

TABLE 1

| Run | Catalyst | Conversion % | Selectivity % |
|---|---|---|---|
| 1 | 5% Pd/Al₂O₃ | 64 | 62 |
| 2 | 5% Pd/CaCO₃ | 7 | 45 |
| 3 | 5% Rh/C | 35 | 80 |
| 4 | 5% Pt/C | 31 | 91 |

EXAMPLE 3

The reaction conditions of Example 1 are substantially repeated employing 0.5 g of 5 percent by weight platinum on carbon catalyst. The reaction is conducted at 35° C. for 10 hours under 250 psig (1723.75 kPa) oxygen atmosphere. Reduction is performed at 120° C. for 2 hours under 40 psig (275.8 kPa) of H₂. Analysis of the product mixture by gas-liquid chromatography shows 85 percent conversion of 2,4,6-trimethylphenol and 89 percent selectivity to 1,2-bis-(3,5-dimethyl-4-hydroxyphenyl)ethane.

EXAMPLE 4

The reaction conditions of Example 3 are substantially repeated employing 1 g of 5 percent by weight palladium on carbon (50 percent water by weight). The oxidation is performed at 25° C. for 14 hours under 350 psig (2413.25 kPa) of O₂. The reduction is performed under hydrogen atmosphere (120° C., 2 hours, 40 psig (275.8 kPa). Analysis of the product by gas-liquid chromatography indicates 80 percent conversion and 83 percent selectivity to the desired 1,2-bis-(3,5-dimethyl-4-hydroxyphenyl)ethane.

EXAMPLE 5

Into a 300-ml stainless steel Parr bomb is placed 25 g of 2,4,6-trimethylphenol, 2.0 g of 5 percent platinum on carbon and 75 ml of acetic acid. The bomb is pressurized to 250 psig with O₂ and heated to 75° C. The bomb is held at this temperature for 4.5 hours. The material is filtered through celite and the acetic acid is removed by rotary evaporation. A 75 percent yield of 3,5-dimethyl-4-hydroxybenzaldehyde is obtained. This material is further purified using a toluene slurry wash (m.p. 111° C.-113° C.). The principle by-product is 2,6-dimethyl p-benzoquinone.

EXAMPLE 6

Into a 300-ml stainless steel Parr bomb is placed 10 g of 2,4,6-trimethylphenol, 1.0 g of 5 percent palladium on carbon (50 percent water by weight) and 30 ml of acetic acid. The bomb is pressurized to 250 psig and heated to 70° C. The reactor is held at this temperature for 2 hours. The bomb is cooled and its contents are filtered through celite. The solvent is removed by rotary evaporation. The solid 3,5-dimethyl-4-hydroxybenzylacetate is recrystallized from toluene in 64 percent yield (8.9 g, m.p. 72° C.–75° C.).

EXAMPLE 7

Into a 300-ml stainless steel stirred autoclave is placed 10 g of 2,4,6-trimethylphenol, 0.5 g of 5 percent platinum on carbon and 30 ml of methacrylic acid. The reactor is pressurized to 250 psig and heated to 50° C. The reactor is held at this temperature for 20 hours. The reaction is discontinued and the mixture is filtered through celite. Analysis by gas-liquid chromatography indicates the product mixture contains 65 percent 3,5-dimethyl-4-hydroxybenzylmethacrylate and 32 percent 3,5-dimethyl-4-hydroxybenzaldehyde.

EXAMPLE 8

Into a 300-ml stainless steel Parr bomb is placed 25 g of 2,4,6-trimethylphenol, 2 g of 5 percent platinum on carbon (wetted with 2 g of $H_2O$) and 60 ml of methanol. The bomb is pressurized to 200 psig with $O_2$ and heated to 110° C. for 15 hours. The reaction can be followed by gas chromatography, observing the initial formation of the 2,6-dimethyl-4-methoxymethylphenol followed by its disappearance and the formation of 3,5-dimethyl-4-hydroxybenzaldehyde. After cooling, the solvent is removed leaving a solid which after purification yields 3,5-dimethyl-4-hydroxybenzaldehyde in 70 percent yield.

EXAMPLE 9

Into a 2-liter stainless steel stirred autoclave is placed 300 g of 2,4,6-trimethyl phenol, 26 g of 5 percent platinum on carbon (wetted with 26 g of $H_2O$) and 800 ml of ethylene glycol. The bomb is pressurized to 220 psig (1500 kPa) with $O_2$ and heated at 80° C. for 6 hours. The reaction can be followed by gas chromatography, observing the initial formation of the 2,6-dimethyl-4-[(2-hydroxyethoxy)methyl]phenol followed by its disappearance and the formation of 3,5-dimethyl-4-hydroxybenzaldehyde. The solution is filtered hot to remove the catalyst. Upon cooling the 3,5-dimethyl-4-hydroxybenzaldehyde precipitates from solution and is isolated by simple filtration. After washing with $H_2O$ to remove traces of ethylene glycol, a 78 percent yield of pure 3,5-dimethyl-4-hydroxybenzaldehyde is obtained (m.p. 112.5° C.–113° C.).

EXAMPLE 10

The reaction procedure of Example 9 is repeated at atmospheric pressure in a stirred glass reactor (stirrer speed equal to 2,000 rpm). The reaction temperature is 80° C., $O_2$ is continuously added by hollow shaft impeller. After 17 hours reaction analysis by gas-liquid chromatography indicates a conversion of about 90 percent. The product is essentially entirely the nucleophilic addition product comprising about 35 percent 3,5-dimethyl-4-hydroxybenzaldehyde and the remainder 2,6-dimethyl-4-[(2-hydroxyethoxy)methyl]phenol.

What is claimed is:

1. A process for oxidizing p-methylsubstituted hindered phenols to selectively prepare oxygenated organic products comprising contacting a p-methyl-substituted hindered phenol with an oxidizing agent and at least a stoichiometric amount of a nucleophile at an elevated temperature in the presence of a catalytic amount of a heterogeneous oxidation catalyst under conditions such that a nucleophile substitution product wherein the nucleophile is substituted on the methyl carbon is selectively prepared.

2. A process according to claim 1 wherein an inert solvent is additionally present.

3. A process according to claim 1 wherein the p-methyl-substituted hindered phenol corresponds to the formula:

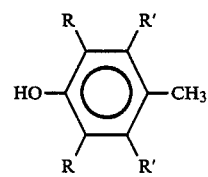

wherein R is independently each occurrence halogen or a substituent of up to 6 carbons selected from the group consisting of alkyl, alkenyl, haloalkyl and alkoxy and R' is independently each occurrence hydrogen, halogen or a substituent of up to 6 carbons selected from the group consisting of alkyl, alkenyl, haloalkyl and alkoxy, and where the selectivity to the nucleophilic substitution product is about 60 percent or greater said nucleophile substitution product being represented by the formula

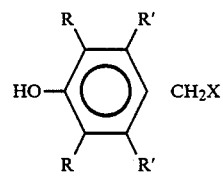

wherein R and R' are as defined hereinbefore and X is a remnant of a nucleophile.

4. A process according to claim 3 wherein the oxidation temperature is from about 25° C. to about 150° C.

5. A process according to claim 3 wherein the heterogeneous oxidation catalyst comprises Ru, Os, Rh, Ir, Pd or Pt.

6. A process according to claim 3 wherein the p-methyl-substituted phenol is 2,4,6-trimethyl phenol, the nucleophile is acetic acid or ethylene glycol, the catalyst is a heterogeneous platinum or palladium on carbon catalyst and the oxidizing agent is gaseous oxygen.

7. A process according to claim 3 wherein the nucleophile is phenol, water, hydrogen cyanide, hydrogen halide, or an aliphatic nucleophilic reagent having up to about 20 carbons selected from the group consisting of carboxylic acids, amines, alcohols and anhydrides.

8. A process according to claim 3 wherein the nucleophile is a carboxylic acid or alcohol.

9. A process according to claim 3 wherein the nucleophile is selected from the group consisting of (poly)alkylene glycols or (poly)alkylene glycol ethers.

10. The process of claim 3 wherein X is a remnant of a nucleophile selected from the group consisting of halo, hydroxy, cyano, —OC(O)alkyl, —OC(O)hydroxyalkyl, —OC(O)alkenyl, —OC(O)aryl, —OC-(O)alkaryl, —OC(O)alkenylaryl, —OC-(O)—(CH$_2$CH$_2$)$_{\overline{n}}$H, —OC(O)—CH$_2$CH—alkyl)$_{\overline{n}}$H, —OC(O)—(CH$_2$CH$_2$)$_n$alkyl, —OC(O)—(CH$_2$CH—alkyl)$_{\overline{n}}$alkyl, —O—alkyl, —O—hydroxyalkyl, —O—alkenyl, —O—aryl, —O—alkaryl, —O—alkenylaryl, —O—(CH$_2$CH$_2$)$_{\overline{n}}$H, —O—(CH$_2$CH—alkyl)$_{\overline{n}}$H, —O—(CH$_2$CH$_2$)$_{\overline{n}}$alkyl and —O—(CH$_2$CH—alkyl)$_{\overline{n}}$alkyl, where each of the carbon-containing moieties is maximally of about 20 carbons.

11. The process of claim 3 wherein the nucleophile substitution product is further oxidized to form a hydroxybenzaldehyde represented by the formula:

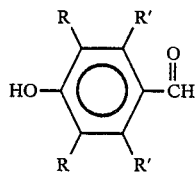

wherein R and R' are as defined in claim 3.

12. A process according to claim 3 wherein the oxidizing agent comprises gaseous oxygen.

13. A process according to claim 12 wherein the oxygen pressure is from about 25 psig (172.375 kPa) to about 1000 psig (6895 kPa).

14. A process according to claim 3 wherein the selectivity is about 70 percent or greater.

15. A process according to claim 14 wherein the nucleophile is ethylene glycol or acetic acid.

16. A process according to claim 14 wherein the selectivity is about 80 percent or greater.

17. A process according to claim 16 wherein the selectivity is about 90 percent or greater.

18. A process for oxidizing p-methyl-substituted hindered phenols to selectively produce a substituted stilbenequinone which process comprises contacting a p-methyl-substituted hindered phenol with an oxidizing agent at an elevated temperature in the presence of a catalytic amount of a heterogeneous oxidation catalyst and in the absence of a nucelophile under conditions such that a substituted stilbenedquinone is selectively prepared.

19. The process according to claim 18 wherein the p-methyl-substituted phenol corresponds to the formula:

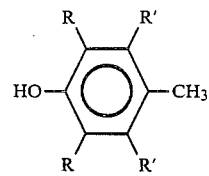

wherein R is independently at each occurrence halogen or a substituent of up to 6 carbons selected from the group consisting of alkyl, alkenyl, haloalkyl and alkoxy provided that when R is the substituent the carbon bonded to the aromatic ring is a primary carbon, the oxidation catalyst is a noble metal oxide and R' is independently at each occurrence hydrogen, halogen or a substituent of up to 6 carbons selected from the group consisting of alkyl, alkenyl, and haloalkyl and the selectivity to the substituted stilbenequinone corresponding to the formula

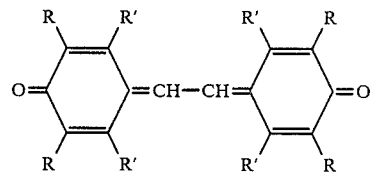

is about 60 percent or greater.

20. The process of claim 17 wherein the noble metal is platinum, palladium, ruthenium, iridium, osmium and rhodium and the selectivity is about 80 percent or greater.

21. The process of claim 19 wherein the noble metal is platinum and the selectivity is about 90 percent or greater.

22. The process of claim 21 wherein the catalyst is platinum on carbon or activated charcoal and the oxidation temperature is from about 25° C. to about 80° C.

23. The process of claim 22 wherein the hindered phenol is 2,4,6-trimethylphenol and the oxidizing agent is a source of elemental oxygen.

24. The process of claim 23 wherein the oxidation temperature is from about 25° C. to about 40° C.; the selectivity is about 80 percent or greater, and the conversion of 2,4,6-trimethyl phenol is about 80 percent or greater.

* * * * *